United States Patent
Sheehan et al.

(10) Patent No.: US 12,252,462 B2
(45) Date of Patent: Mar. 18, 2025

(54) METHOD AND APPARATUS FOR SELECTIVE ALCOHOL UPGRADING

(71) Applicant: Air Company Holdings, Inc., Brooklyn, NY (US)

(72) Inventors: Stafford W Sheehan, Tiverton, RI (US); Chi Chen, Shrewsbury, MA (US); Nicholas J. Steinke, Brooklyn, NY (US)

(73) Assignee: Air Company Holdings, Inc., Brooklyn, NY (US)

(*) Notice: Subject to any disclaimer, the term of this patent is extended or adjusted under 35 U.S.C. 154(b) by 0 days.

(21) Appl. No.: 18/626,650

(22) Filed: Apr. 4, 2024

(65) Prior Publication Data
US 2024/0246894 A1    Jul. 25, 2024

Related U.S. Application Data

(60) Division of application No. 18/349,315, filed on Jul. 10, 2023, now Pat. No. 11,981,623, which is a (Continued)

(51) Int. Cl.
*C07C 29/17* (2006.01)
*B01D 3/14* (2006.01)
(Continued)

(52) U.S. Cl.
CPC ........... *C07C 29/172* (2013.01); *B01D 3/14* (2013.01); *B01J 8/0419* (2013.01); *B01J 21/04* (2013.01);
(Continued)

(58) Field of Classification Search
CPC . B01J 8/0419; B01J 21/04; B01J 23/06; B01J 23/72; B01J 23/80; B01D 3/14;
(Continued)

(56) References Cited

U.S. PATENT DOCUMENTS

| 719,623 A | 2/1903 | Spohn |
| 1,873,536 A | 8/1932 | Brown et al. |

(Continued)

FOREIGN PATENT DOCUMENTS

| CA | 2496839 A1 | 1/2006 |
| CN | 114939433 A | 8/2022 |

(Continued)

OTHER PUBLICATIONS

Chen et al., "Single-Step Production of Alcohols and Paraffins from CO2 and H2 at Metric Ton Scale," ACS Energy Letters, 7: pp. 988-992 (2022).

(Continued)

*Primary Examiner* — Jafar F Parsa
(74) *Attorney, Agent, or Firm* — Foley Hoag LLP; Lucas P. Watkins; Lucas A. Freeman

(57) ABSTRACT

Methods for utilizing carbon dioxide to produce multi-carbon products are disclosed. The systems and methods of the present disclosure involve: reducing $CO_2$ to produce a first product mixture comprising an alcohol product mixture comprising one or more alcohols and a paraffin product mixture comprising one or more paraffins; dehydrating the alcohol product mixture to form an olefin product mixture comprising one or more olefins; oligomerizing the olefin product mixture to form a higher olefin product mixture comprising unsaturated paraffins and optionally aromatics; and reducing the higher olefin product mixture to form a higher hydrocarbon product mixture comprising unsaturated paraffins and optionally aromatics. Catalyst materials and reaction conditions for individual steps are disclosed to optimize yield for ethanol or jet fuel range hydrocarbons.

18 Claims, 9 Drawing Sheets

Related U.S. Application Data continuation of application No. PCT/US2022/029834, filed on May 18, 2022.

(60) Provisional application No. 63/189,826, filed on May 18, 2021.

(51) Int. Cl.
| | |
|---|---|
| *B01J 8/04* | (2006.01) |
| *B01J 21/04* | (2006.01) |
| *B01J 23/06* | (2006.01) |
| *B01J 23/72* | (2006.01) |
| *B01J 23/80* | (2006.01) |
| *C07C 1/24* | (2006.01) |
| *C07C 2/12* | (2006.01) |
| *C07C 5/27* | (2006.01) |
| *C07C 29/154* | (2006.01) |
| *C10G 47/20* | (2006.01) |

(52) U.S. Cl.
CPC .............. *B01J 23/06* (2013.01); *B01J 23/72* (2013.01); *B01J 23/80* (2013.01); *C07C 1/24* (2013.01); *C07C 2/12* (2013.01); *C07C 5/277* (2013.01); *C07C 29/154* (2013.01); *C10G 47/20* (2013.01); *C07C 2529/40* (2013.01); *C07C 2529/72* (2013.01); *C10G 2400/08* (2013.01)

(58) Field of Classification Search
CPC .. C07C 1/24; C07C 2/12; C07C 5/277; C07C 29/154; C07C 2529/72; C07C 2529/40; C10G 47/20; C10G 2400/08
See application file for complete search history.

(56) References Cited

U.S. PATENT DOCUMENTS

| | | | |
|---|---|---|---|
| 3,452,106 | A | 6/1969 | Sato et al. |
| 4,482,767 | A | 11/1984 | Imai |
| 4,499,327 | A | 2/1985 | Kaiser |
| 5,126,308 | A | 6/1992 | Barger et al. |
| 5,714,662 | A | 2/1998 | Vora et al. |
| 7,772,448 | B2 | 8/2010 | Clark et al. |
| 8,436,215 | B2 | 5/2013 | Chornet et al. |
| 8,779,215 | B2 | 7/2014 | Kharas |
| 9,663,416 | B2 | 5/2017 | Lilga et al. |
| 9,932,531 | B2 | 4/2018 | Lilga et al. |
| 10,464,859 | B2 | 11/2019 | Ge et al. |
| 10,472,573 | B2 | 11/2019 | Ge et al. |
| 11,827,593 | B2 | 11/2023 | Peters et al. |
| 11,958,041 | B2 | 4/2024 | Sheehan et al. |
| 11,981,623 | B2 | 5/2024 | Sheehan et al. |
| 12,018,221 | B2 | 6/2024 | Zhou et al. |
| 2003/0220531 | A1 | 11/2003 | Cortright et al. |
| 2005/0107481 | A1 | 5/2005 | Janssen et al. |
| 2007/0187291 | A1 | 8/2007 | Miller et al. |
| 2011/0105630 | A1 | 5/2011 | Dorner et al. |
| 2012/0209037 | A1 | 8/2012 | Viljoen et al. |
| 2013/0030224 | A1 | 1/2013 | Kim et al. |
| 2014/0051897 | A1 | 2/2014 | Peters et al. |
| 2015/0175505 | A1 | 6/2015 | Glover et al. |
| 2015/0247100 | A1 | 9/2015 | Bradin |
| 2016/0038919 | A1 | 2/2016 | Landau et al. |
| 2017/0327757 | A1 | 11/2017 | Abhari et al. |
| 2018/0362426 | A1 | 12/2018 | Chen et al. |
| 2019/0071374 | A1 | 3/2019 | Ge et al. |
| 2019/0194559 | A1 | 6/2019 | Mdleleni et al. |
| 2021/0147326 | A1 | 5/2021 | Sheehan |
| 2022/0184586 | A1 | 6/2022 | Yao et al. |
| 2023/0001389 | A1 | 1/2023 | Ong et al. |
| 2023/0060945 | A1 | 3/2023 | Sheehan |
| 2023/0069964 | A1 | 3/2023 | Littlewood et al. |
| 2023/0348347 | A1 | 11/2023 | Sheehan et al. |
| 2023/0390744 | A1 | 12/2023 | Sheehan et al. |
| 2024/0124792 | A1 | 4/2024 | Zhou et al. |
| 2024/0216895 | A1 | 7/2024 | Sheehan et al. |
| 2024/0246894 | A1 | 7/2024 | Sheehan et al. |

FOREIGN PATENT DOCUMENTS

| | | | |
|---|---|---|---|
| CN | 118056609 | A | 5/2024 |
| EP | 0096996 | A2 | 12/1983 |
| EP | 0269297 | A1 | 6/1988 |
| SG | 2013051370 | A | 12/2014 |
| WO | WO-2019/010095 | A1 | 1/2019 |
| WO | WO-2021/262922 | A1 | 12/2021 |
| WO | WO-2022/008534 | A1 | 1/2022 |
| WO | WO-2022/245944 | A1 | 11/2022 |
| WO | WO-2023/137002 | A1 | 7/2023 |
| WO | WO-2024/064384 | | 3/2024 |
| WO | WO-2024/064387 | | 3/2024 |
| WO | WO-2024/081844 | A1 | 4/2024 |

OTHER PUBLICATIONS

Choi et al., "Sodium-Containing Spinel Zinc Ferrite as a Catalyst Precursor for the Selective Synthesis of Liquid Hydrocarbon Fuels", *ChemSusChem* 10.23: 4764-4770 (2017).

International Search Report and Written Opinion for International Application No. PCT/US2023/033544 dated Jan. 2, 2024.

International Search Report and Written Opinion for International Application No. PCT/US23/76782 dated Feb. 15, 2024.

International Search Report and Written Opinion for International Application No. PCT/US2022/029834 dated Oct. 11, 2022.

International Search Report and Written Opinion for International Application No. PCT/US2023/033547 dated Dec. 4, 2023.

International Search Report and Written Opinion for International Application No. PCT/US23/10444 dated Apr. 13, 2023.

Liang et al., "Direct conversion of CO2 to aromatics over K-Zn-Fe/ZSM-5 catalysts via a Fischer-Tropsch synthesis pathway." *Industrial & Engineering Chemistry Research* 61.29: 10336-10346 (2022).

Xu et al., "Ternary Fe—Zn—Al spinel catalyst for CO2 hydrogenation to linear α-olefins: synergy effects between Al and Zn", *ACS Sustainable Chemistry & Engineering* 9.41: 13818-13830 (2021).

Zhang et al., "Zn and Na promoted Fe catalysts for sustainable production of high-valued olefins by CO2 hydrogenation", *Fuel* 309: 122105 (2022).

Zhou et al., "Direct carbon dioxide hydrogenation to produce bulk chemicals and liquid fuels via heterogeneous catalysis." *Chinese Journal of Catalysis* 43(8) (2022): 2045-2056.

METHOD AND APPARATUS FOR SELECTIVE ALCOHOL UPGRADING

CROSS-REFERENCE TO RELATED APPLICATIONS

This application is Divisional of U.S. patent application Ser. No. 18/349,315, filed Jul. 10, 2023; which is a Continuation of International Patent Application No. PCT/US22/29834, filed May 18, 2022; which claims the benefit of priority to U.S. Provisional Patent Application No. 63/189,826, filed May 18, 2021, the contents of each of which are incorporated herein by reference in their entirety.

BACKGROUND

As the concentration of carbon dioxide in the atmosphere increases, it is advantageous to develop technologies that remove or mitigate carbon dioxide emissions. Countries are rapidly adopting regulations against greenhouse gas (GHG) emissions, and specifically $CO_2$, due to the negative effects toward social welfare, human health, and energy security that increased atmospheric $CO_2$ concentrations cause. This adds an additional economic incentive for businesses to produce and utilize large commodity scale products from $CO_2$, rather than emitting it into the atmosphere.

The need for removing $CO_2$ from the air is coupled with an increasing global utilization of renewable electricity generation methods, such as solar photovoltaics and wind turbines. Renewable electricity generation methods emit fewer greenhouse gases per kilowatt-hour generated than electricity generation via fossil fuels, such as coal and natural gas. Therefore, from a $CO_2$ removal perspective, it is advantageous to use renewable or other low-carbon electricity to power processes the utilize $CO_2$. While there are several chemical technologies that utilize $CO_2$ as a reagent, hydrogenation of carbon dioxide using hydrogen gas holds potential to produce lower-carbon chemicals than several of its competitors. Hydrogen can be generated from a water electrolyzer, as it can be powered completely by renewable electricity, or by other methods that produce carbon neutral hydrogen gas, such as steam methane reforming combined with carbon sequestration.

A need exists for scalable processes for $CO_2$ utilization and conversion to products containing greater than one carbon atom, such as higher alcohols or hydrocarbon fuels, as these generally have greater economic value than those that contain fewer carbon atoms, in part due to their complexity to produce. While processes exist that convert $CO_2$ into molecules such as carbon monoxide, methane, and methanol, there is a need for chemical processes capable of upgrading these single carbon products into multi-carbon alcohols and hydrocarbons. These higher alcohols and hydrocarbons can enable economic $CO_2$ utilization to make products that result in lower $CO_2$ equivalent emissions than their fossil fuel-derived counterpart.

SUMMARY

In some aspects, provided herein are systems for the production of alcohols or hydrocarbons, comprising:
a $CO_2$ reduction reactor for converting a first gas mixture comprising $CO_2$ and a reduction gas to a first product mixture comprising an alcohol product mixture comprising one or more alcohols and optionally a paraffin product mixture comprising one or more paraffins; wherein the $CO_2$ reduction reactor comprises a first catalyst;
an ATO reactor for dehydrating the alcohol product mixture into an olefin product mixture comprising one or more olefins; wherein the ATO reactor comprises a second catalyst;
an oligomerization reactor for oligomerizing the olefin product mixture to a higher olefin product mixture comprising unsaturated paraffins and optionally aromatics; wherein the oligomerization reactor comprises a third catalyst; and
an olefin reduction reactor for reducing the higher olefin product mixture to a higher hydrocarbon product mixture comprising unsaturated paraffins, wherein the olefin reduction reactor comprises a fifth catalyst.

In certain embodiments, the system further comprises:
a separator configured to separate ethylene from the olefin product mixture;
a combination vessel for combining the ethylene with water to form a third feed mixture; and
an ethylene hydration reactor for hydrating the ethylene to form ethanol, wherein the ethylene hydration reactor comprises a fourth catalyst.

In further embodiments, the ethylene hydration reactor is configured such that a mixture of ethylene and steam pass through a dispersed catalyst contact and reaction zone.

In further aspects, provided herein are methods for the conversion of $CO_2$ to alcohols or hydrocarbons, comprising:
reducing $CO_2$ to a first product mixture comprising:
an alcohol product mixture comprising one or more alcohols; and
a paraffin product mixture comprising one or more paraffins;
said reducing step comprising contacting a first gas mixture comprising the $CO_2$ and a reduction gas with a first catalyst at a reduction temperature and a reduction pressure;
optionally separating the alcohol product mixture from the paraffin product mixture;
dehydrating the alcohol product mixture into an olefin product mixture comprising one or more olefins, said dehydrating step comprising contacting the alcohol product mixture with a second catalyst at an ATO temperature and an ATO pressure;
oligomerizing the olefin product mixture to a higher olefin product mixture comprising unsaturated paraffins and optionally aromatics, said oligomerizing step comprising contacting the olefin product mixture with a third catalyst at an oligomerization temperature and an oligomerization pressure; and
reducing the higher olefin product mixture to a higher hydrocarbon product mixture
comprising unsaturated paraffins, said reducing step comprising contacting the higher olefin product mixture with a fifth catalyst at a olefin reduction temperature and an olefin reduction pressure.

In certain embodiments, the method further comprises:
separating ethylene from the olefin product mixture;
forming a third feed mixture comprising ethylene and water;
hydrating the ethylene in the third feed mixture, said hydrating step comprising contacting the third feed mixture with a fourth catalyst at an ethylene hydration temperature and an ethylene hydration pressure to produce ethanol.

In yet further aspects, provided herein are methods for the conversion of $CO_2$ to ethanol, comprising:

contacting a first gas mixture comprising $CO_2$ and a reduction gas with a first catalyst at a reduction temperature and a reduction pressure to produce a first product mixture comprising methanol and ethanol;

contacting a second feed mixture comprising methanol with a second catalyst at an MTO temperature and an MTO pressure to produce ethylene and a second product mixture comprising $C_3$ and higher paraffins, olefins, and other hydrocarbons; wherein the MTO pressure is an ATO pressure, and the MTO temperature is an ATO temperature;

optionally, contacting the second product mixture comprising $C_3$ and higher paraffins, olefins, and other hydrocarbons with a third catalyst at a Jet-A temperature and a Jet-A pressure to produce jet fuel; wherein the Jet-A pressure is an olefin reduction pressure, and the Jet-A temperature is an olefin reduction temperature;

contacting a third feed mixture comprising ethylene and water with a fourth catalyst at an ethylene hydration temperature and an ethylene hydration pressure to produce ethanol.

DETAILED DESCRIPTION

Figure 1:
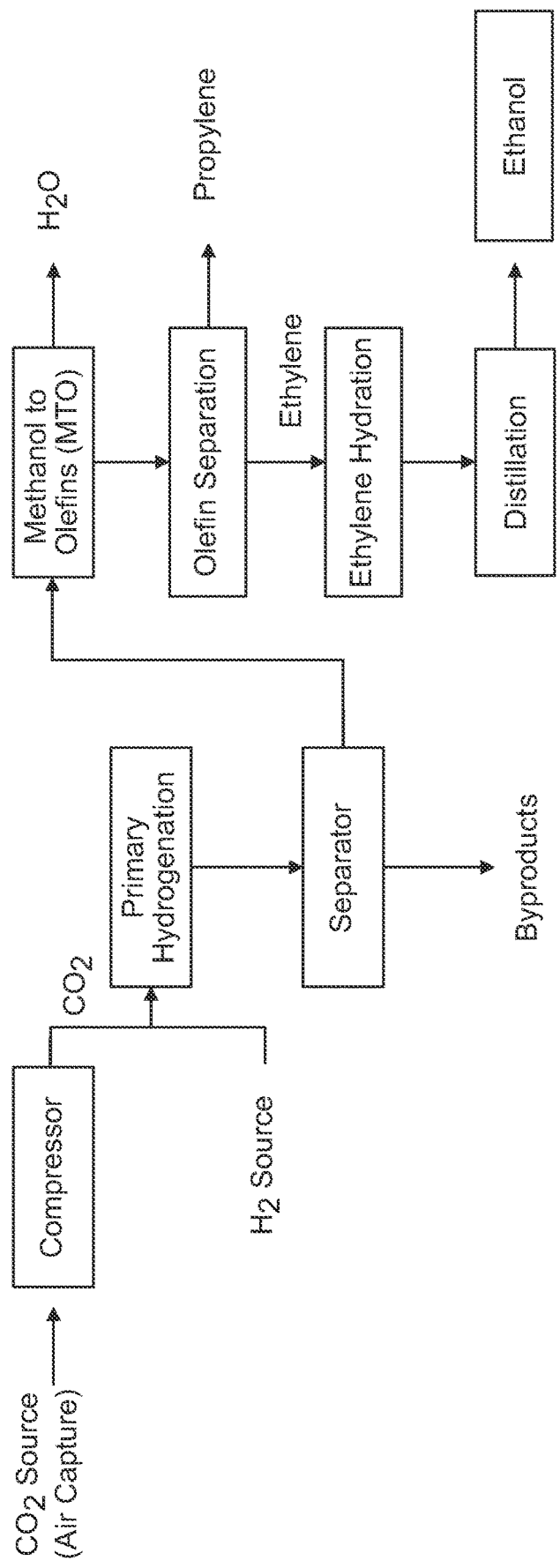
FIG. 1 shows a process schematic of the system for coproduction of jet fuel and ethanol.
Figure 2:
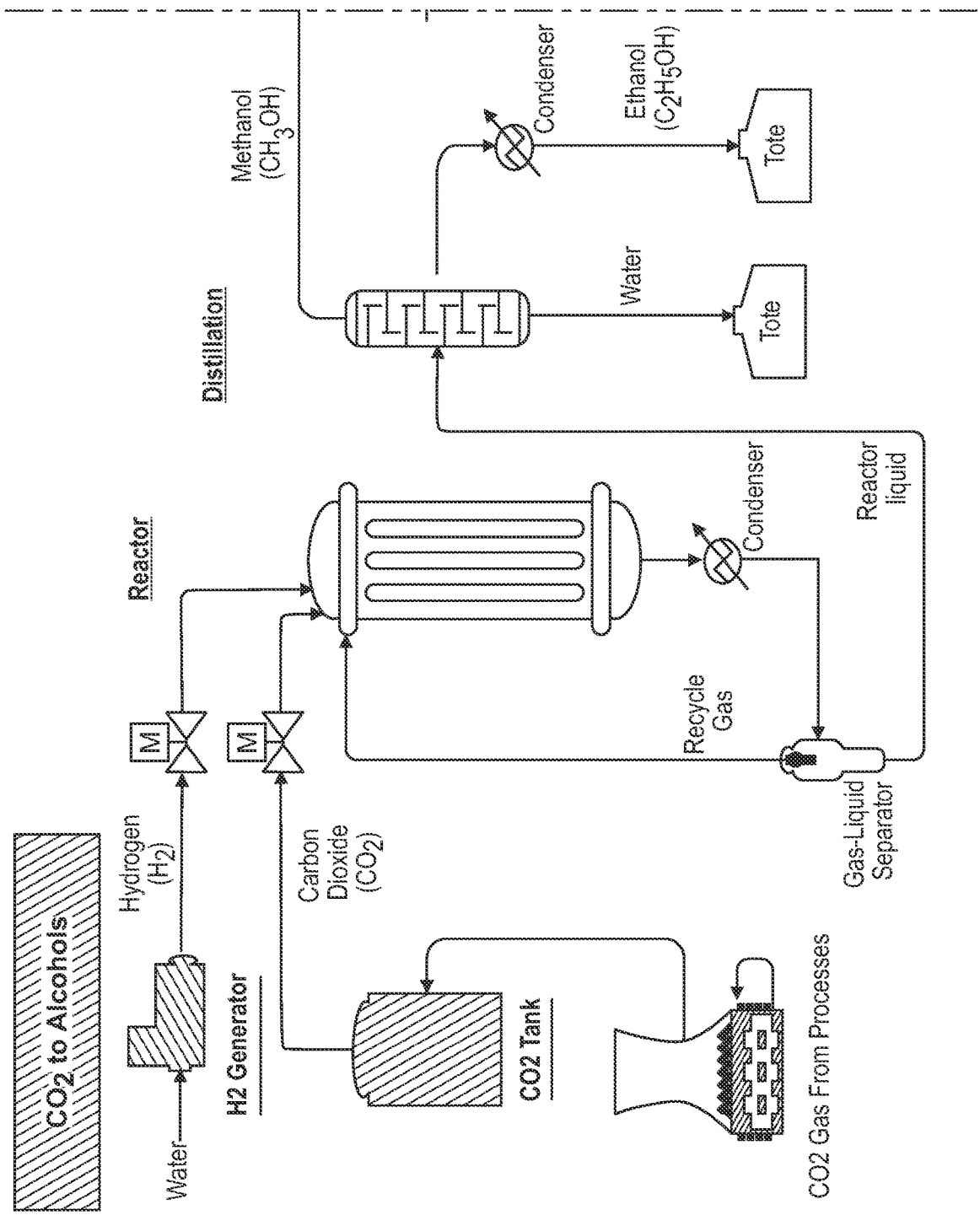
FIG. 2 shows a flow diagram depicting components and reactors for a system that converts carbon dioxide and water into ethanol and propylene powered by renewable energy.
Figure 2:
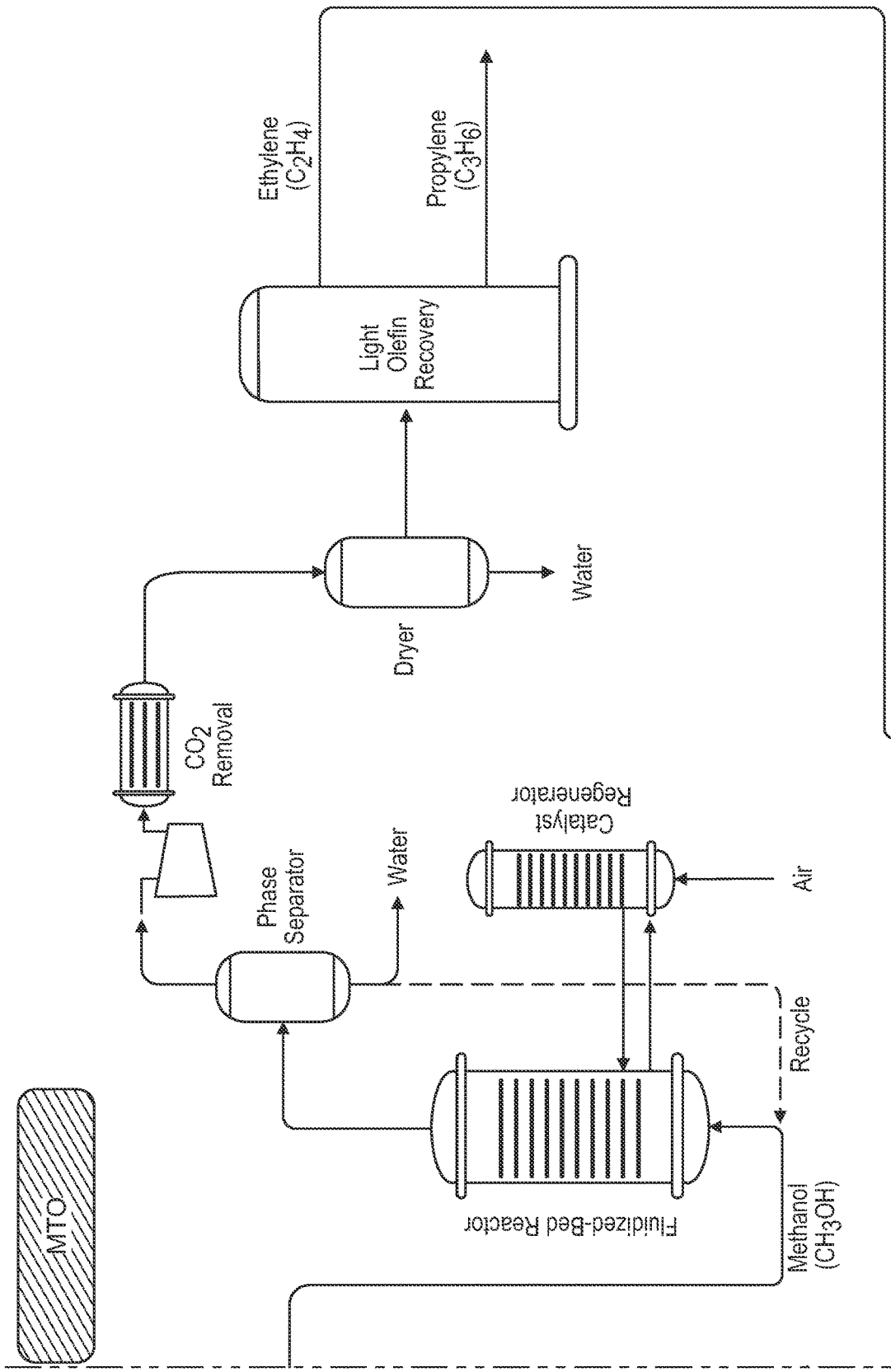
Figure 2:
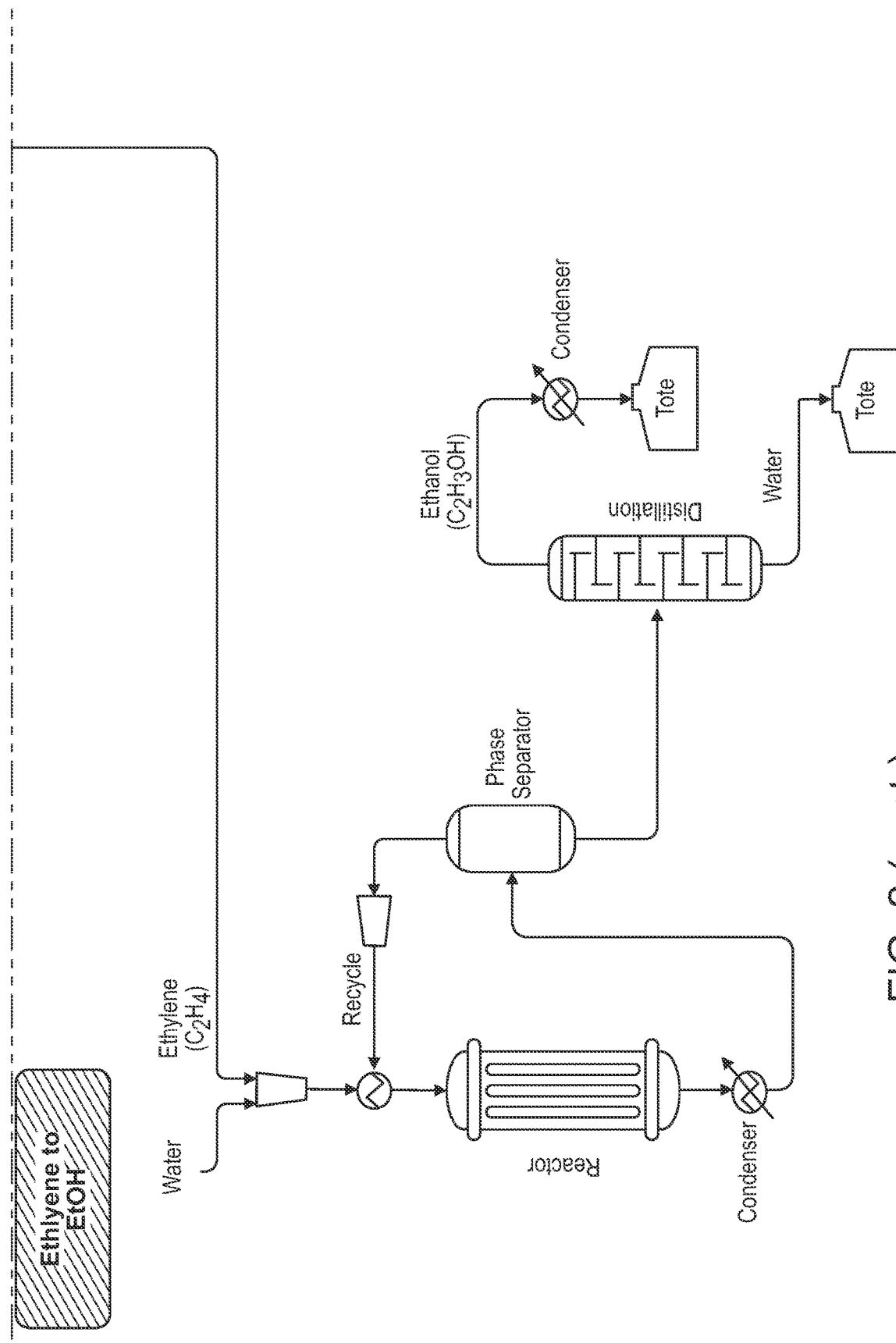
Figure 3:
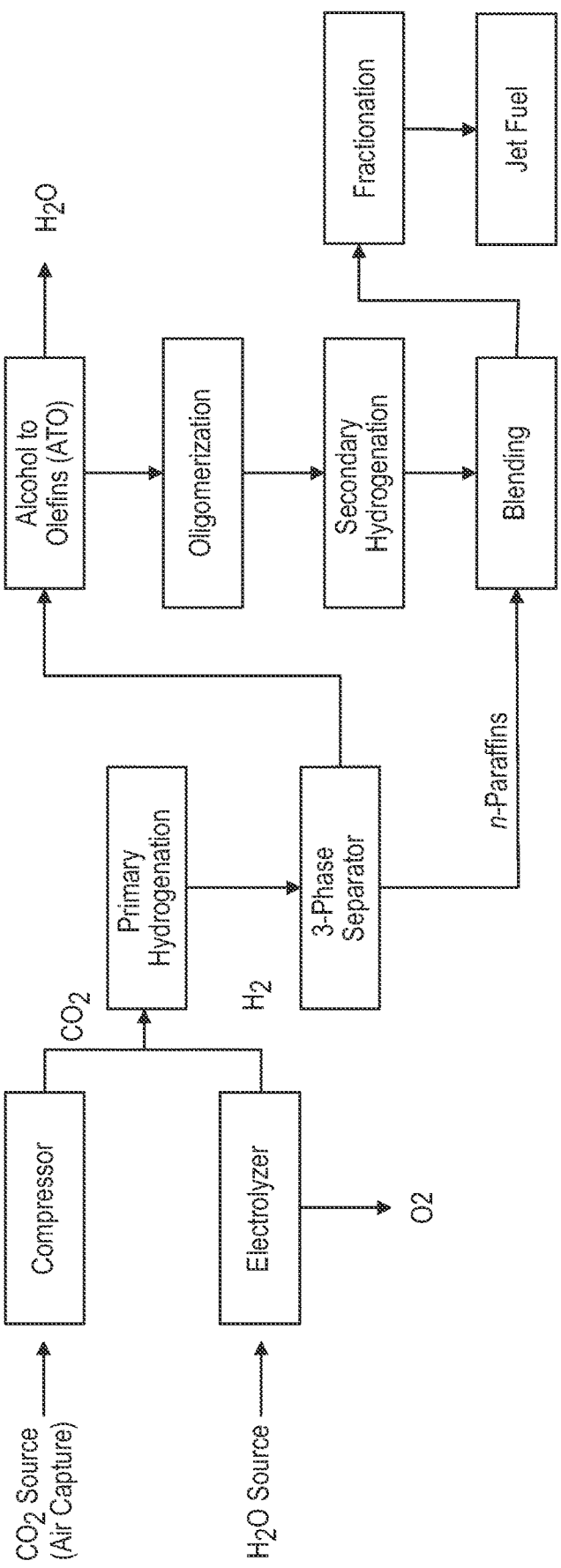
FIG. 3 shows a flow diagram depicting components and reactors for a system that converts carbon dioxide and water into a drop-in sustainable aviation fuel comprising both aromatics and paraffins.

In certain aspects, the present disclosure provides systems and methods for conversion of $CO_2$ to alcohols and hydrocarbons. In some embodiments of the present invention, $CO_2$ is sourced from capture from a point source and optionally purified using an amine capture system or other purification system, and in others the $CO_2$ is captured from the air. In some embodiments, the $CO_2$ is used in the form of flue gas. The systems and methods of the present disclosure can be used regardless of the source of $CO_2$.

Description of Overall Process

In certain aspects, the systems and methods of the present disclosure operate through the following steps: reducing $CO_2$ to produce a first product mixture comprising an alcohol product mixture comprising one or more alcohols and a paraffin product mixture comprising one or more paraffins; dehydrating the alcohol product mixture to form an olefin product mixture comprising one or more olefins; oligomerizing the olefin product mixture to form a higher olefin product mixture comprising unsaturated paraffins and optionally aromatics; and reducing the higher olefin product mixture to form a higher hydrocarbon product mixture comprising unsaturated paraffins and optionally aromatics. As will be understood by one of skill in the art, the terms "higher olefins" and "unsaturated paraffins" are synonymous, and are used interchangeably herein. The first product mixture, which includes both the alcohol and paraffin product mixtures, may be separated into its alcohol and paraffin components before subjecting the alcohol product mixture to the dehydration step, or the entire first product mixture may be processed through the dehydration step. If the separation step occurs, the alcohol product mixture may be reintroduced at any suitable stage in the overall process, or in a subsequent blending step. Each reaction occurs within a reactor that is suitable for that particular reaction, including the presence of a suitable catalyst. The present disclosure encompasses both the overall process (in which the steps of the process may be carried out in any suitable order), and systems in which each reactor is operationally coupled to the subsequent reactor such that the product from each step is transported to the subsequent reactor for the subsequent reaction t.

Those of skill in the art will also recognize that separation steps may be added at any suitable stage, either to optimize a product of any step for the reaction of the subsequent step, or to isolate useful products. For example, in certain embodiments, the alcohol product mixture created in the initial reduction step comprises ethanol. The ethanol may be isolated from the alcohol product mixture (or first product mixture) and retained for sale or other disposition. The remainder of the alcohol product mixture (or first product mixture) may then be processed through the remaining steps. Other useful products include ethylene (which may be separated after the dehydration step) and aromatics (which may be separated after the oligomerization step).

Accordingly, in certain aspects, provided herein are systems for the production of alcohols or hydrocarbons, comprising:

a $CO_2$ reduction reactor for converting $CO_2$ to a first product mixture comprising an alcohol product mixture comprising one or more alcohols and optionally a paraffin product mixture comprising one or more paraffins; wherein the $CO_2$ reduction reactor comprises a first catalyst;

an ATO reactor for dehydrating the alcohol product mixture into an olefin product mixture comprising one or more olefins; wherein the ATO reactor comprises a second catalyst;

an oligomerization reactor for oligomerizing the olefin product mixture to a higher olefin product mixture comprising unsaturated paraffins and optionally aromatics; wherein the oligomerization reactor comprises a third catalyst; and an olefin reduction reactor for reducing the higher olefin product mixture to a higher hydrocarbon product mixture comprising unsaturated paraffins, wherein the olefin reduction reactor comprises a fifth catalyst.

In further aspects, provided herein are methods for the conversion of $CO_2$ to alcohols or hydrocarbons, comprising:

reducing $CO_2$ to a first product mixture comprising:
an alcohol product mixture comprising one or more alcohols; and
a paraffin product mixture comprising one or more paraffins;

said reducing step comprising contacting a first gas mixture comprising the $CO_2$ and a reduction gas with a first catalyst at a reduction temperature and a reduction pressure;

optionally separating the alcohol product mixture from the paraffin product mixture;

dehydrating the alcohol product mixture into an olefin product mixture comprising one or more olefins, said dehydrating step comprising contacting the alcohol product mixture with a second catalyst at an ATO temperature and an ATO pressure;

oligomerizing the olefin product mixture to a higher olefin product mixture comprising unsaturated paraffins and optionally aromatics, said oligomerizing step comprising contacting the olefin product mixture with a third catalyst at an oligomerization temperature and an oligomerization pressure; and reducing the higher olefin product mixture to a higher hydrocarbon product mixture comprising unsaturated paraffins, said reducing step comprising contacting the higher olefin product mixture with a fifth catalyst at a olefin reduction temperature and an olefin reduction pressure.

In yet further aspects, provided herein are methods for the conversion of $CO_2$ to ethanol, comprising:

contacting a first gas mixture comprising $CO_2$ and a reduction gas with a first catalyst at a reduction temperature and a reduction pressure to produce a first product mixture comprising methanol and ethanol;

contacting a second feed mixture comprising methanol with a second catalyst at an MTO temperature and an MTO pressure to produce ethylene and a second product mixture comprising $C_3$ and higher paraffins, olefins, and other hydrocarbons; wherein the MTO pressure is an ATO pressure, and the MTO temperature is an ATO temperature;

optionally, contacting the second product mixture comprising $C_3$ and higher paraffins, olefins, and other hydrocarbons with a third catalyst at a Jet-A temperature and a Jet-A pressure to produce jet fuel; wherein the Jet-A pressure is an olefin reduction pressure, and the Jet-A temperature is an olefin reduction temperature;

contacting a third feed mixture comprising ethylene and water with a fourth catalyst at an ethylene hydration temperature and an ethylene hydration pressure to produce ethanol.

$CO_2$ Capture

In certain embodiments of the presently disclosed systems and methods, the $CO_2$ utilized can be captured from ambient air. Methods for this $CO_2$ capture are described in International Application No. PCT/US2022/021469, the entire content of which is expressly incorporated by reference herein.

In certain embodiments, the systems of the present disclosure comprise an apparatus for carbon dioxide capture comprising an solution of a zinc complex in water and optionally a co-solvent; wherein the zinc complex comprises at least one ligand coordinated to zinc.

In certain embodiments, the methods of the present disclosure comprise capturing carbon dioxide from a gas feed stream, comprising contacting the gas feed stream with a solution of a zinc complex in water and optionally a co-solvent to react the carbon dioxide with water to form a solution of hydrated carbon dioxide, thereby forming a solution of hydrated carbon dioxide; wherein the zinc complex comprises at least one ligand coordinated to zinc.

In certain embodiments, the at least one ligand is a bidentate, tridentate, tetradentate, pentadentate, hexadentate, heptadentate, or octadentate ligand coordinated to zinc in at least a $\kappa^2$ fashion. In further embodiments, the at least one ligand is not a cyclen or porphyrin ligand.

In certain embodiments, the zinc complex has the formula:

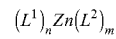

wherein:

each $L^1$ is a bidentate, tridentate, tetradentate, pentadentate, hexadentate, heptadentate, or octadentate ligand coordinated to Zn in at least a $\kappa^2$ fashion;

each $L^1$ is bound to Zn through at least one donor heteroatom selected from O or N;

each $L^1$ is mono-, di-, tri-, tetra-, penta-, or hexaanionic;

each $L^2$ is selected from —OH or —OH$_2$;

n is 1 or 2; and m is 0 or 1.

In further embodiments, the zinc complex further comprises a cation, the complex having the formula:

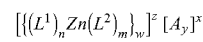

wherein:

z is the charge of the $\{(L^1)_n Zn(L^2)_m\}$ fragment, and is selected from 0, −1, −2, or −3;

A is a cation;

x is the charge of the A cation, and is selected from +1 or +2;

w is an integer equal to (y·x)/z; and y is an integer equal to (w·z)/x.

In yet further embodiments, $L^1$ is not a cyclen or porphyrin ligand. In still further embodiments, $L^1$ is selected from ethylenediaminetetraacetic acid (EDTA), glutaric acid, nitrilotriacetic acid, triazacyclononane, trispyrazolylborate, terpyridine, porphine, corrin, tris(2-aminoethyl)amine, triethylenetetramine, 12-crown-4, 15-crown-5, 16-crown-6, (2,2,2)cryptand, glycine, salen, 2-(pyridine-2-yl)propan-2-ol, niacin, picolinic acid, 2-acetylpyridine, iminodiacetic acid, oxalate, glutaric acid, ethylene glycol-bis(β-aminoethyl ether)-N,N,N',N'-tetraacetic acid (EGTA), diethylenetriaminepentaacetic acid, or ethylenediamine-N,N'-bis(2-hydroxyphenylacetic acid) (EDDHA), each of which may be optionally substituted by one or more substituents independently selected from H, OH, amino, imine, sulfate, sulfonyl, alkyl, heteroalkyl, alkoxy, aryl, heteroaryl, cycloalkyl, heterocycloalkyl, acetyl, carboxylate, or glycolate.

In certain embodiments, $L^1$ is a ligand of Formula $L^{1A}$, $L^{1B}$, $L^{1C}$, or $L^{1D}$:

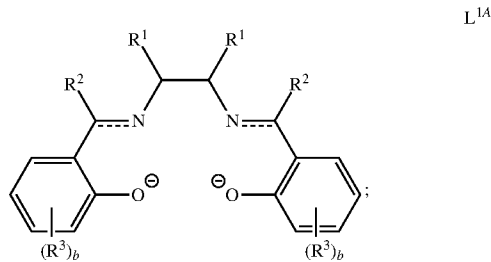

-continued

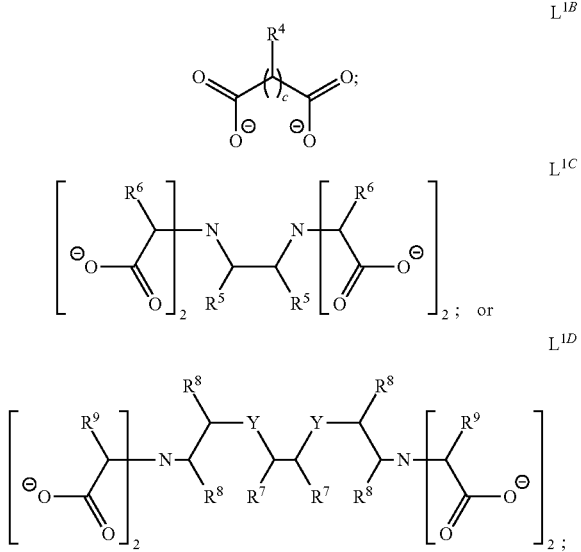

wherein:
each $R^1$, $R^2$, $R^3$, $R^4$, $R^5$, $R^6$, $R^7$, $R^8$, and $R^9$ is, independently at each occurrence, selected from H, OH, amino, imine, sulfate, sulfonyl, alkyl, heteroalkyl, alkoxy, aryl, heteroaryl, cycloalkyl, heterocycloalkyl, acetyl, carboxylate, glycolate;
Y is NH, S, or O;
b is, independently at each occurrence, an integer from 0-4;
c is, independently at each occurrence, an integer from 0-3; and
=== is a single or double bond.
In further embodiments, $L^1$ is selected from:

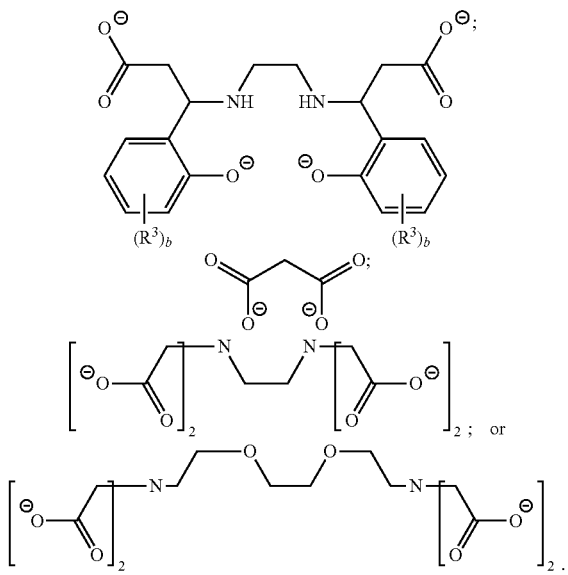

In yet further embodiments, the cation is selected from ammonium, sodium, potassium, calcium, or magnesium. In still further embodiments, the complex is soluble in water, and wherein the complex is stable under basic conditions. In certain embodiments, the complex is stable at a pH from about 7 to about 16. In further embodiments, the complex is stable at a pH from about 8 to about 10.

In certain embodiments, the solution of a zinc complex further comprises a salt. In further embodiments, the salt is a carbonate salt. In yet further embodiments, the salt is potassium carbonate. In still further embodiments, the salt is present in the solution in an amount of about 0.001 M to about 20 M. In certain embodiments, the zinc complex is present in the solution in an amount of about 0.00001 M to about 10 M. In further embodiments, the pH of the solution is from about 7 to about 16. In yet further embodiments, the pH of the solution is from about 8 to about 10.

In certain embodiments, the co-solvent is selected from ethanolamine, propylene carbonate, or an ionic liquid. In further embodiments, the solution of the zinc complex is homogeneous.

$CO_2$ Hydrogenation to Alcohols and Paraffins

The presently disclosed systems and methods are particularly useful for the conversion of $CO_2$ to paraffins and alcohols. As used herein, the term "paraffin" is used to refer to long-chain hydrocarbons, preferably $C_8$-$C_{16}$ hydrocarbons, which may be linear, branched, cyclic, or a mixture thereof. Paraffins may also be fully saturated, fully unsaturated, partially saturated, partially unsaturated, or a mixture thereof.

Any suitable catalyst for the hydrogenation of $CO_2$ to alcohols may be used in the methods described herein. Exemplary catalysts for the hydrogenation of $CO_2$ to alcohols which are suitable for the presently disclosed systems and methods are disclosed in the following applications, each of which is incorporated by reference in its entirety: PCT Publication Nos. WO 2021/226172, WO 2021/262922, and WO 2019/010095.

In some embodiments, in the first reactor $CO_2$ and $H_2$ are passed over a catalyst or catalysts to produce a mixture of methanol, ethanol, and other alcohols. In some embodiments, $CO_2$ and $H_2$ are passed over a catalyst or catalysts to produce substantially pure methanol (i.e., 80%, 85%, 90%, 95%, 99%, etc.). The most common catalyst for this type of process is a copper-based catalyst. Several other materials are capable of producing mixtures of methanol and ethanol, including but not limited to modified CuZnAl catalysts that include Co, Fe, or Ni, zirconia-based catalysts, CoS, MoS, CoMoS, CoMoSK, NiCoMoSK, and several others.

In certain embodiments, the catalyst for $CO_2$ hydrogenation, referred to herein as the "first catalyst," comprises platinum, palladium, copper, cobalt, zinc, selenium, rhodium, iron, molybdenum, sulfur, oxygen, or alloys or chemical compounds thereof. In further embodiments, the first catalyst comprises nanoparticles comprising CuZn, CuZnFeK, CuZnFeKC, CuZnFeAlK, CuZnFeNa, CuZnFeCoK, CuZnFeCoNaK, CuCoAl, CoMoSK, CuZnK, CuCoMn, RhRu, PdCuFe, Rh, or RhFeSi, optionally on an alumina support. In yet further embodiments, the first catalyst comprises nanoparticles comprising CoMoSK, optionally on an alumina support.

In certain embodiments, the first catalyst comprises:
molybdenum;
one or more first elements selected from a Group V, VI, VII, VIII, IX, X, and XI metal (e.g., silver, cobalt, nickel, copper, rhodium, ruthenium, iridium, palladium, niobium, and manganese);
one or more second elements selected from sulfur, carbon, oxygen, phosphorus, nitrogen, and selenium; and
optionally, one or more Group IA metals,
wherein the molybdenum is present in an amount of 10-50 wt. % of the total amount of the one or more first elements, the molybdenum, the one or more second elements, and the Group IA metal.

In certain embodiments, the one or more first elements comprise silver, cobalt, nickel, copper, rhodium, ruthenium, iridium, palladium, niobium, or manganese. In further embodiments, the one or more first elements comprise cobalt. In yet further embodiments, the one or more first elements comprise nickel. In still further embodiments, the one or more first elements comprise silver. In certain embodiments, the one or more first elements comprise copper. In further embodiments, the one or more first elements comprise niobium. In yet further embodiments, the one or more first elements comprise manganese.

In certain embodiments, the first catalyst comprises the one or more first elements at a molar ratio of about 0.15 to about 2 relative to the molybdenum. In further embodiments, the first catalyst comprises cobalt at a molar ratio of about 0.15 to about 2 relative to the molybdenum. In yet further embodiments, the first catalyst comprises cobalt at a molar ratio of about 0.29 relative to the molybdenum. In still further embodiments, the first catalyst comprises nickel at a molar ratio of about 0.15 to about 2 relative to the molybdenum. In certain embodiments, the first catalyst comprises nickel at a molar ratio of about 0.36 relative to the molybdenum. In further embodiments, the first catalyst comprises silver at a molar ratio of about 0.15 to about 2 relative to the molybdenum. In yet further embodiments, the first catalyst comprises silver at a molar ratio of about 1 relative to the molybdenum. In still further embodiments, the first catalyst comprises one or more Group IA metals.

In certain embodiments, the one or more Group IA metals comprise potassium. In further embodiments, the one or more Group IA metals comprise sodium. In yet further embodiments, the one or more Group IA metals comprise cesium. In still further embodiments, the first catalyst comprises the one or more Group IA metals at a molar ratio from about 0.10 to about 0.50 relative to molybdenum. In certain embodiments, the first catalyst comprises the one or more Group IA metals to molybdenum at a molar ratio of about 0.44 relative to molybdenum.

In certain embodiments, the one or more Group IA metals comprise potassium. In further embodiments, the first catalyst comprises the one or more second elements at a molar ratio from about 0.3 to about 3.25 relative to molybdenum. In yet further embodiments, the first catalyst comprises the one or more second elements at a molar ratio from about 3 to about 3.25 relative to molybdenum. In still further embodiments, the first catalyst comprises the one or more second elements at a molar ratio from about 2.5 to about 3.25 relative to molybdenum. In certain embodiments, the one or more second elements comprise sulfur.

In certain embodiments, the one or more second elements comprise carbon. In further embodiments, the first catalyst comprises sulfur at a molar ratio of about 3.25 relative to molybdenum. In yet further embodiments, the first catalyst comprises silver, molybdenum, sulfur, and a Group IA metal.

In certain embodiments, the first catalyst comprises:
molybdenum;
silver at a molar ratio of about 1 relative to the molybdenum;
sulfur at a molar ratio of about 3 relative to the molybdenum; and
the Group IA at a molar ratio of about 0.4 relative to the molybdenum.

In further embodiments, the first catalyst comprises nickel, cobalt, molybdenum, sulfur, and a Group IA metal.

In certain embodiments, the first catalyst comprises:
molybdenum;
nickel at a molar ratio of about 0.36 relative to the molybdenum;
cobalt at a molar ratio of about 0.29 relative to the molybdenum;
sulfur at a molar ratio of about 3.25 relative to the molybdenum; and
the Group IA at a molar ratio of about 0.44 relative to the molybdenum.

In further embodiments, the first catalyst comprises niobium, cobalt, molybdenum, sulfur, and a Group IA metal.

In certain embodiments, the first catalyst comprises:
niobium at a molar ratio of about 0.12 relative to the molybdenum;
cobalt at a molar ratio of about 0.6 relative to the molybdenum;
sulfur at a molar ratio of about 3.25 relative to the molybdenum; and
the Group IA at a molar ratio of about 0.4 relative to the molybdenum.

In further embodiments, the first catalyst comprises:
copper;
zinc;
one or more first elements selected from cobalt, nickel, or iron;
aluminum;
oxygen;
optionally, one or more second elements selected from a Group V, VI, VII, VIII, IX, X, and XI metal (e.g., manganese, silver, niobium, zirconium, molybdenum, ruthenium, or palladium); and
optionally, one or more Group IA metals, and wherein the cobalt is present in an amount of about 10 to about 40 wt. % (e.g., about 25 to about 40 wt. %, about 30 to about 40 wt. %, or about 35 to about 40 wt. %) of the total amount of the copper, zinc, cobalt, the optional first element, and the optional Group IA metal.

In certain embodiments, the first catalyst comprises the one or more second elements. In further embodiments, the one or more first elements comprise iron. In yet further embodiments, the one or more first elements comprise nickel. In still further embodiments, the one or more second elements comprise manganese. In certain embodiments, the one or more second elements comprise zirconium. In further embodiments, the one or more second elements comprise niobium. In yet further embodiments, the one or more second elements comprise molybdenum.

In certain embodiments, the first catalyst comprises copper at a molar ratio of about 1 to about 3 relative to the first element. In further embodiments, the first catalyst comprises copper at a molar ratio of about 2 to about 2.5 relative to the first element. In yet further embodiments, the first catalyst comprises zinc at a molar ratio of about 0.5 to about 1.5 relative to the first element. In still further embodiments, the first catalyst comprises iron at a molar ratio of about 0.5 to about 1.5 relative to the first element. In certain embodiments, the first catalyst comprises aluminum at a molar ratio of about 0.4 to about 2.1 relative to first element. In further embodiments, the first catalyst comprises aluminum at a molar ratio of about 0.5 to about 1 relative to first element.

In certain embodiments, the first catalyst comprises one or more Group IA metals. In further embodiments, the one or more Group IA metals comprise potassium. In yet further embodiments, the one or more Group IA metals comprise sodium. In still further embodiments, the one or more Group IA metals comprise cesium. In certain embodiments, the first catalyst comprises the one or more Group IA metals at a molar ratio from about 0.05 to about 0.5 relative to the first element. In further embodiments, the first catalyst comprises the one or more Group IA metals at a molar ratio of about 0.15 relative to the first element.

In certain embodiments, the first catalyst comprises zinc oxide. In further embodiments, the first catalyst comprises copper oxide. In yet further embodiments, the first catalyst comprises cobalt oxide. In still further embodiments, the first catalyst comprises alumina.

In certain embodiments, the first catalyst comprises cobalt, copper, zinc oxide, and alumina. In further embodiments, the first catalyst comprises:
  copper at a molar ratio of about 2.5 relative to the cobalt;
  zinc oxide at a molar ratio of about 1 relative to the cobalt; and
  alumina at a molar ratio of about 0.35 relative to the cobalt.

In certain embodiments, the first catalyst comprises cobalt, copper, zinc oxide, alumina, and a Group IA metal. In further embodiments, the first catalyst comprises:
  copper at a molar ratio of about 2.5 relative to the cobalt;
  zinc oxide at a molar ratio of about 1 relative to the cobalt;
  alumina at a molar ratio of about 0.35 relative to the cobalt; and
  the Group IA metal at a molar ratio of about 0.1 relative to the cobalt.

In certain embodiments, the first catalyst comprises cobalt, iron, copper, zinc oxide, alumina, and a Group IA metal. In further embodiments, the first catalyst comprises:
  copper at a molar ratio of about 1 relative to the cobalt;
  iron at a molar ratio of about 1 relative to the cobalt;
  zinc oxide at a molar ratio of about 1 relative to the cobalt;
  alumina at molar ratio of about 0.35 relative to the cobalt; and
  the Group IA metal at a molar ratio of about 0.1 relative to the cobalt.

In certain embodiments, the first catalyst further comprises a support. In further embodiments, the support comprises one or more materials selected from an oxide, nitride, fluoride, or silicate of an element selected from aluminum, silicon, titanium, zirconium, cerium, magnesium, yttrium, lanthanum, zinc, and tin. In yet further embodiments, the support comprises γ-alumina. In still further embodiments, the support comprises one or more carbon-based material. In certain embodiments, the carbon-based material is selected from activated carbon, carbon nanotubes, graphene, and graphene oxide. In further embodiments, the support is a mesoporous material. In yet further embodiments, the support has a mesopore volume from about 0.01 to about 3.0 cc/g. In still further embodiments, the support has surface area from about 10 m$^2$/g to about 1000 m$^2$/g.

In certain embodiments, the first catalyst is in a form of particles having an average size from about 20 nm to about 5 μm. In further embodiments, the first catalyst is in a form of particles having an average size from about 50 nm to about 1 μm. In yet further embodiments, the first catalyst is in a form of particles having an average size from about 100 nm to about 500 nm. In still further embodiments, the first catalyst is in a form of particles having an average size from about 50 nm to about 300 nm.

In certain embodiments, the first catalyst is embedded in a monolith, pressed into pellets or extruded into a morphology that supports it under reaction conditions.

In certain embodiments, the reduction gas is $H_2$. In further embodiments, the reduction gas is a hydrocarbon, such as $CH_4$, ethane, propane, or butane. In yet further embodiments, the reduction gas is, or is derived from, flare gas, waste gas, or natural gas. In still further embodiments, the reduction gas is $CH_4$.

In certain embodiments, the molar ratio of reduction gas:$CO_2$ in the first gas mixture is from about 10:1 to about 1:10. In further embodiments, the molar ratio of reduction gas:$CO_2$ in the first gas mixture is about 5:1 to about 0.5:1.

In certain embodiments, the first product mixture comprises methanol, ethanol, and n-propanol. In further embodiments, the amount of ethanol is at least 10 wt. % of the total amount of first product mixture. In yet further embodiments, the molar ratio of ethanol to the total amount of methanol and n-propanol in the first product mixture is from about 1:5 to about 1:10.

In certain embodiments, the amount of formic acid in the first product mixture is less than 10 ppm. In further embodiments, the amount of isopropanol in the first product mixture is less than 10 ppm.

In certain embodiments, the first catalyst is contacted with the first gas mixture for 24 hours. In further embodiments, the first catalyst is contacted with the first gas mixture for 96 hours. In yet further embodiments, the first catalyst is contacted with the first gas mixture for 168 hours. In certain embodiments, the first catalyst is reacted with the reduction gas prior to reacting with the first gas mixture.

The temperature of this reactor, referred to herein as the "reduction temperature," is typically 250° C., but may be has high as 600° C. or as low as 50° C. In certain embodiments, the reduction temperature is from about 100° C. to about 600° C. In further embodiments, the reduction temperature is about 100° C. In yet further embodiments, the reduction temperature is about 200° C. In preferred embodiments, the reduction temperature is about 250° C. In certain embodiments, the reduction temperature is about 300° C. In further embodiments, the reduction temperature is about 400° C. In yet further embodiments, the reduction temperature is about 500° C. In still further embodiments, the reduction temperature is about 600° C.

The pressure of this reactor, referred to herein as the "reduction pressure," can be between 100 psi and 3000 psi, but is typically 750 psi. In certain embodiments, the reduction pressure is from about 500 psi to about 3000 psi. In further embodiments, the reduction pressure is about 500 psi. In preferred embodiments, the reduction pressure is about 750 psi. In further embodiments, the reduction pressure is about 100 psi. In further embodiments, the reduction pressure is about 1500 psi. In further embodiments, the reduction pressure is about 2000 psi. In further embodiments, the reduction pressure is about 2500 psi. In further embodiments, the reduction pressure is about 3000 psi.

As will be appreciated by one of skill in the art, measurement of pressure in the unit "pounds per square inch" (psi) can refer to either the pressure measured on a gauge (psig), where 0 psi corresponds to atmospheric pressure, or the absolute pressure (psia), where 0 psi corresponds to a perfect vacuum. As used herein, unless the contrary is explicitly specified, the unit "psi" refers to gauge pressure (psig).

Following conversion of $CO_2$ and $H_2$ into alcohols and water, unreacted feedstock as well as gas phase alcohol and water are cooled in a condenser loop and separated in a gas-liquid separator. Unreacted gases are passed through a recycle loop to combine with fresh feedstock and re-introduced into the reactor. Per-pass conversion for the reactor is typically around 20%, but can range from 1% to 99.9% depending on gas hourly space velocity (GHSV) of feedstock gases, catalyst reactivity, pressure, and temperature.

In certain embodiments, following conversion of $CO_2$ to alcohols, the ethanol can be separated from the remainder of the alcohol products. Additionally, following conversion of $CO_2$ to alcohols, the alcohol product mixture can be separated from the paraffin product mixture.

Conversion of Alcohols to Olefins

In some embodiments, following alcohol production, a typical liquid produced by the first step of this process would be comprised of water along with alcohols. The alcohols would be comprised primarily of methanol, secondarily of ethanol, and may have several other tertiary byproducts including n-propanol. In some embodiments, the mixture contains up to 20% methanol and up to 20% ethanol. In some embodiments, the mixture contains up to 64% methanol. In some embodiments, the mixture contains up to 15% methanol and up to 3% ethanol. It is an object of the present invention to disclose optimized liquid concentrations for integration of the methanol production from $CO_2$ reaction and methanol to olefins reaction. The weight ratio of alcohols to water is a key parameter that helps to determine olefin selectivity and activity for the methanol to olefins process.

In some embodiments, the alcohol and water mixture from the first reactor is condensed into a liquid. In some embodiments, the alcohol and water mixture from the first reactor is passed into the second reactor in the vapor phase. In some embodiments, the liquid alcohol and water mixture is heated to over 100° C. so that all components of it are vaporized for introduction into the methanol to olefins reactor.

Catalysts for the conversion of alcohols to olefins which are suitable for the presently disclosed systems and methods are disclosed in the following patents, each of which is incorporated by reference in its entirety: EP Patent No. 0,096,996; U.S. Pat. Nos. 4,499,327; 5,191,141; 5,126,308; 5,714,662; and 4,440,871.

The methods and systems of the present disclosure can include this conversion step being carried out on either the complete first product mixture (i.e., containing both alcohols and paraffins), or solely the alcohol product mixture.

The methanol to olefin reactor is typically a fixed bed flow reactor, but may be one of several other reactor types, including a trickle bed reactor, a fluidized bed reactor, an ebullated bed reactor, a continuously stirred tank reactor, or others. The methanol to olefin reactor includes a catalyst that converts methanol into olefins such as ethylene, propylene, butylenes, and others at elevated temperature and ambient to low pressures.

In some embodiments, the alcohol to olefin (ATO) catalyst or methanol to olefin (MTO) catalyst comprises fluid catalyst particles comprising a crystalline zeolite or a silicoaluminophosphate. In further embodiments, the ATO or MTO catalyst comprises SAPO-5, H-SAPO-34, ZSM-11, TNU-9, IM-5, ZSM-35, ZSM-22, ZSM-23, SSZ-13, UZM-12, UZM-9, UZM-5, RUB-13, ZSM-5, or ZSM-34.

In some embodiments, the ATO or MTO catalyst comprises a transition metal-promoted silicoaluminophosphate, such as Ni-SAPO-34. In some embodiments, the ATO or MTO catalyst comprises KIT-6 or transition metal-promoted KIT-6. In some embodiments, the ATO or MTO catalyst is an acidic catalyst with active sites that assist in the coordination and insertion of methanol to selectively produce olefins with water as a byproduct. In some embodiments, nickel or other transition metals are used to promote oligomerization.

In certain embodiments, the ATO or MTO reactor is configured such that a suspension of vaporized methanol and the fluid catalyst particles pass upwardly through a dispersed catalyst contact and reaction zone.

In certain embodiments, the ATO or MTO temperature is from about 260° C. to about 510° C. In further embodiments, the ATO or MTO temperature is from about 315° C. to about 370° C. In yet further embodiments, the ATO or MTO temperature is about 315° C. In preferred embodiments, the ATO or MTO temperature is about 325° C. In certain embodiments, the ATO or MTO temperature is about 335° C. In further embodiments, the ATO or MTO temperature is about 345° C. In yet further embodiments, the ATO or MTO temperature is about 355° C. In still further embodiments, the ATO or MTO temperature is about 365° C. In certain embodiments, the ATO or MTO temperature is about 370° C.

In certain embodiments, the ATO or MTO pressure is from about 100 kPa to about 515 kPa. In preferred embodiments, the ATO or MTO pressure is about 100 kPa. In certain embodiments, the ATO or MTO pressure is about 200 kPa. In further embodiments, the ATO or MTO pressure is about 300 kPa. In yet further embodiments, the ATO or MTO pressure is about 400 kPa. In still further embodiments, the ATO or MTO pressure is about 500 kPa. In certain embodiments, the ATO or MTO pressure is about 515 kPa.

In some embodiments, 90-100% of the methanol is converted to olefins. In some embodiments, ethylene is the preferred product of the MTO or ATO reaction. In some embodiments, the reaction is performed at ambient pressure. The resulting olefins are separated from byproduct water and purified by distillation, membrane separation, or any other technique for separating olefins known to those skilled in the art. In some embodiments, the resulting ethylene is purified to 90%. In some embodiments, the resulting ethylene is purified to 99.9%. In some embodiments, the resulting ethylene is purified to 99.99% or higher.

Ethylene Hydration

In some embodiments, the ethylene product from the alcohol to olefins reactor is separated and fed into an ethylene hydration reactor. The ethylene hydration reactor is typically a fixed bed flow reactor but may be one of several other reactor types. In the ethylene hydration reactor, the ethylene is mixed with steam at a ratio of about 0.6 $H_2O$:$C_2H_4$, though the ratio may vary depending on the catalyst used. The steam and ethylene are heated to a temperature between 100 and 300° C., typically 250° C. for phosphoric acid on silica catalysts.

In certain embodiments, the system further comprises:
a separator configured to separate ethylene from the olefin product mixture;
a combination vessel for combining the ethylene with water to form a third feed mixture; and
an ethylene hydration reactor for hydrating the ethylene to form ethanol, wherein the ethylene hydration reactor comprises a fourth catalyst.

In further embodiments, the ethylene hydration reactor is configured such that a mixture of ethylene and steam pass through a dispersed catalyst contact and reaction zone.

In certain embodiments, the method further comprises:
separating ethylene from the olefin product mixture;
forming a third feed mixture comprising ethylene and water;
hydrating the ethylene in the third feed mixture, said hydrating step comprising contacting the third feed mixture with a fourth catalyst at an ethylene hydration temperature and an ethylene hydration pressure to produce ethanol.

Catalysts for ethylene hydration which are suitable for the presently disclosed systems and methods are disclosed in the following patents, each of which is incorporated by reference in its entirety: U.S. Pat. Nos. 1,873,536; 3,452,106; and 4,482,767.

Catalysts for the ethylene hydration reaction, which are referred to in as the "fourth catalyst," include, but are not limited to, phosphoric acid on silica, phosphoric acid on carbon, zeolites such as H-ZSM-5 or H-Beta, acidic polysiloxanes, polytungstate acids, or metal phosphides such as germanium, titanium, tin, and silicon phosphide.

In certain embodiments, the fourth catalyst is a resin-type catalyst. In further embodiments, the fourth catalyst is a sulfonated styrene-divinylbenzene copolymer resin or phosphoric acid on silica gel.

In some embodiments, the $C_{3+}$ products of the alcohol to olefins reaction will be used to produce larger hydrocarbons in a fixed bed flow reactor. In some embodiments, the ethylene along with the $C_{3+}$ products of the alcohol to olefins reaction will be used to produce larger hydrocarbons. This reaction occurs in a fuel synthesis reactor, containing an acidic zeolite such as H-ZSM-5, and, unlike the alcohol to olefins process, the olefins are both heated and pressurized to temperatures of about 100° C. to 400° C., preferably 250° C. and pressures of about 100 psi to 2000 psi, preferably 1000 psi. The flow rate and per-pass conversion through the reactor are controlled to select for hydrocarbons in the $C_8$ to $C_{16}$ or $C_{10}$ to $C_{20}$ range, suitable for use as fuel.

In certain embodiments, the ethylene hydration temperature is from about 100° C. to about 400° C. In further embodiments, the ethylene hydration temperature is about 100° C. In yet further embodiments, the ethylene hydration temperature is about 200° C. In preferred embodiments, the ethylene hydration temperature is about 250° C. In certain embodiments, the ethylene hydration temperature is about 300° C. In further embodiments, the ethylene hydration temperature is about 400° C.

In certain embodiments, the ethylene hydration pressure is from about 500 psi to about 1500 psi. In further embodiments, the ethylene hydration pressure is about 500 psi. In preferred embodiments, the ethylene hydration pressure is about 1000 psi. In certain embodiments, the ethylene hydration pressure is about 1500 psi.

Olefin Oligomerization

In some embodiments, it is desirable to oligomerize the olefins produced from the alcohol to olefins or methanol to olefins process in the presence of an oligomerization catalyst (referred to herein as the "third catalyst") to produce a mixture of higher olefins and optionally aromatics. As used herein, the modifier "higher" with respect to hydrocarbons or olefins will refer to hydrocarbons or olefins with a higher number of carbons than a precursor. Exemplary higher hydrocarbons and olefins include, but are not limited to $C_8$-$C_{16}$ hydrocarbons and/or olefins. Said oligomerization process can be carried out in a fixed bed flow reactor, or any other suitable reactor type.

In certain embodiments, the third catalyst is a zeolite. In further embodiments, the third catalyst is an aluminosilicate zeolite. In yet further embodiments, the third catalyst is selected from ZSM-5, ZSM-11, ZSM-22, ZSM-23, and ZSM-35. In preferred embodiments, the third catalyst is ZSM-5.

The temperature at which this oligomerization can be carried out can range from about 50° C. to about 1000° C. as needed to tailor the degree of oligomerization based on the desired product length and distribution. In certain embodiments, the oligomerization temperature is from about 50° C. to about 1000° C. In further embodiments, the oligomerization temperature is about 50° C. In yet further embodiments, the oligomerization temperature is about 150° C. In preferred embodiments, the oligomerization temperature is about 250° C. In certain embodiments, the oligomerization temperature is about 350° C. In further embodiments, the oligomerization temperature is about 450° C. In yet further embodiments, the oligomerization temperature is about 550° C. In still further embodiments, the oligomerization temperature is about 650° C. In certain embodiments, the oligomerization temperature is about 750° C. In further embodiments, the oligomerization temperature is about 850° C. In yet further embodiments, the oligomerization temperature is about 950° C. In still further embodiments, the oligomerization temperature is about 1000° C.

The pressure at which this oligomerization can be carried out can range from about 0 psi to about 2000 psi as needed to tailor the degree of oligomerization based on the desired product length and distribution. In certain embodiments, the oligomerization pressure is from about 0 psi to about 2000 psi. In further embodiments, the oligomerization pressure is about 0 psi. In further embodiments, the oligomerization pressure is about 0 psi. In preferred embodiments, the oligomerization pressure is about 30 psi. In certain embodiments, the oligomerization pressure is about 250 psi. In further embodiments, the oligomerization pressure is about 500 psi. In yet further embodiments, the oligomerization pressure is about 750 psi. In still further embodiments, the oligomerization pressure is about 1000 psi. In certain embodiments, the oligomerization pressure is about 1250 psi. In further embodiments, the oligomerization pressure is about 1500 psi. In yet further embodiments, the oligomerization pressure is about 1750 psi. In still further embodiments, the oligomerization pressure is about 2000 psi.

In certain embodiments, the higher olefin product mixture produced during the oligomerization step comprises from about 10% to about 20% aromatics by volume.

Hydrogenation of Higher Olefins to Higher Hydrocarbons

Certain aspects of the systems and method disclosed herein involve hydrogenation of the higher olefin product mixture to reduce the number of unsaturated carbon-carbon bonds, and thereby afford a mixture of higher hydrocarbons. As will be appreciated, many catalysts may be suitable for such a hydrogenation. As used herein, the term "fifth catalyst" refers to the catalyst for this hydrogenation reaction.

Additionally, this transformation can be carried out in any suitable reactor type, but the systems and methods disclosed herein typically utilize a fixed bed flow reactor. In certain embodiments, the olefin reduction reactor is configured such that pressurized higher olefin mixture passes through a dispersed catalyst contact and reaction zone.

In certain embodiments, the fifth catalyst is an aluminosilicate catalyst. In further embodiments, the fifth catalyst is H-ZSM-5.

In certain embodiments, the olefin reduction temperature is from about 100° C. to about 400° C. In certain embodiments, the olefin reduction temperature is about 100° C. In further embodiments, the olefin reduction temperature is about 200° C. In preferred embodiments, the olefin reduction temperature is about 250° C. In certain embodiments, the olefin reduction temperature is about 300° C. In further embodiments, the olefin reduction temperature is about 400° C.

In certain embodiments, the olefin reduction pressure is from about 0 psi to about 1500 psi. In certain embodiments, the olefin reduction pressure is about 0 psi. In further embodiments, the olefin reduction pressure is about 500 psi.

In preferred embodiments, the olefin reduction pressure is about 1000 psi. In certain embodiments, the olefin reduction pressure is about 1500 psi.

Conversion of Paraffins to Jet Fuel

In some embodiments, the $C_3$ and higher paraffins, olefins, and other hydrocarbons produced by the methanol to olefins process can be converted into jet fuel.

Catalysts for the conversion of olefins to heavier hydrocarbons suitable for use as jet fuel which are suitable for the presently disclosed systems and methods are disclosed in the following patents, each of which is incorporated by reference in its entirety: U.S. Pat. Nos. 5,210,347; 4,504,693; 4,456,781; 4,834,949; 5,177,279; and PCT Publication No. WO 2001/062875.

In certain aspects of the present disclosure, an apparatus can be used to blend the higher hydrocarbon product mixture, optionally with the paraffin product mixture to create a blended paraffin product mixture.

Additionally, in certain aspects of the present disclosure, it can be beneficial to isomerize some of the linear paraffins and/or linear higher hydrocarbons to afford an isomerized paraffin product mixture comprising linear paraffins, branched paraffins, and cyclic paraffins. Such an isomerization can be accomplished using any suitable catalyst, preferably those referred to herein as the "sixth catalyst." In certain embodiments, the sixth catalyst is a zeolite or $AlCl_3$. In further embodiments, the sixth catalyst is $AlCl_3$. Additionally, this isomerization can take place in any suitable reactor, but is preferably carried out in a continuously stirred tank reactor.

The presently disclosed systems and methods can also comprise an additional apparatus for fractionating the blended paraffin mixture to produce jet fuel. In certain embodiments, the jet fuel produced comprises from about 10% to about 20% aromatics by volume.

DEFINITIONS

Unless otherwise defined herein, scientific and technical terms used in this application shall have the meanings that are commonly understood by those of ordinary skill in the art.

Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-30 for straight chains, $C_3$-30 for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

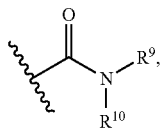

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

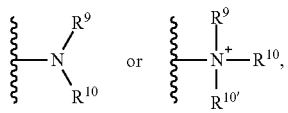

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

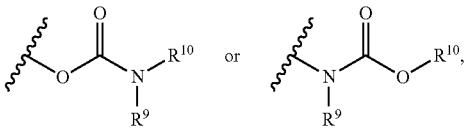

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —$OCO_2$—.

The term "carboxy", as used herein, refers to a group represented by the formula —$CO_2H$.

The term "ester", as used herein, refers to a group —C(O)$OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

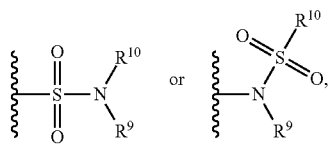

wherein $R^9$ and $R^{10}$ independently represents hydrogen or hydrocarbyl.

The term "sulfoxide" is art-recognized and refers to the group -S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

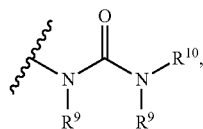

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

As used herein, the term "hydrated carbon dioxide" encompasses all reaction products from the reaction of gaseous carbon dioxide with water in the presence of a catalyst, including, without limitation, carbonic acid, carbonate salts and/or ions, and bicarbonate salts and/or ions.

EXAMPLES

The invention now being generally described, it will be more readily understood by reference to the following examples which are included merely for purposes of illustration of certain aspects and embodiments of the present invention, and are not intended to limit the invention.

Example 1: Conversion of $CO_2$ and $H_2$ to Methanol in a Fixed Bed Flow Reactor $CO_2$ hydrogenation was performed in a fixed bed flow reactor with approximately 9 liters of internal volume. The flow reactor was loaded with 10 kilograms of a catalyst comprised of 63% by weight copper oxide, 27% by weight zinc oxide, and 10% by weight aluminum oxide and pressed into cylinders with 6 mm height and 4 mm diameter. The reactor was heated to approximately 300° C. while $H_2$ gas was flowed through the reactor at a flow rate of 30 standard liters per minute (SLPM) at a pressure of 100 psi to activate the catalyst. Water was collected at the separator downstream from the flow reactor during this activation time. Following catalyst activation, the temperature of the reactor was decreased to 250° C. and pressure was increased to 750 psi. $H_2$ and $CO_2$ were flowed through the reactor at flow rates of 30 SLPM and 10 SLPM, respectively. The gases were reacted at the surface of the catalyst to produce approximately 0.4 liters per hour of a methanol water mixture with a density of 0.89 g/mL, corresponding to approximately 64% methanol in water, thus achieving quantitative selectivity for methanol production. Unreacted gases were recycled through the reactor by way of a recycle loop and compressor to improve the yield for methanol production.

Example 2: General Procedure for Conversion of Methanol to Olefins

Methanol dehydration to produce ethylene, propylene, and other hydrocarbons is accomplished in a fixed bed flow reactor. The flow reactor is loaded with 10 kg of a silicoaluminophosphate catalyst, H-SAPO-34, which is a chabazite structured material comprised of 50% by weight aluminum oxide, 30-45% by weight phosphorous oxide, and 20-5% by weight silicon oxide. The reactor is heated to a temperature of 450° C. A feed mixture of 40% methanol and 60% water is heated to over 180° C. to vaporize the methanol and water, then is introduced to the reactor at 50 PSI and a weight hourly space velocity of 5.0 $h^{-1}$. The methanol is converted to a mixture of ethylene, propylene, butenes, pentenes, paraffins, olefins, and aromatics, with the major product being ethylene which is separated from other products by distillation.

Example 3: General Procedure for Conversion of Olefins to Jet Fuel

A mixture of $C_3$ and higher paraffins, olefins, and other hydrocarbons are converted into jet fuel in a fixed bed flow reactor. The mixture of $C_3$ and higher hydrocarbon feedstock is the product of a methanol to olefins system, with the ethylene removed by distillation. The flow reactor is loaded with 10 kg of an aluminosilicate catalyst, H-ZSM-5, comprised of aluminum oxide and silicon oxide at an approximate ratio of 70:1 silica to alumina. The reactor is heated to approximately 250° C. The mixture of $C_3$ and higher hydrocarbons is pressurized to approximately 30-1000 psi and introduced to the reactor. The flow rate of the $C_3$ and higher hydrocarbon feed is controlled to achieve approximately 50% by weight conversion per pass through the reactor to result in a mixture of $C_8$-$C_{16}$ hydrocarbons. The $C_8$-$C_{16}$ hydrocarbons are distilled to remove heavier fraction of paraffin wax resulting in a hydrocarbon liquid with energy density approximately 11.3 kWh/L and otherwise suitable as jet fuel.

Example 4: Olefins Formation from Methanol-to-Olefin Process

To a 1-in diameter flow reactor was loaded with 15 g of a H-SAPO-34 catalyst pelletized in cylinder of 7.6 mm diameter and 2.5 mm thickness. Nitrogen was fed into the reactor at 0.1 SLPM. The system was flushed with $N_2$ for 15 minutes before slowly increase the furnace temperature to 450° C. A liquid mixture directly collected from $CO_2$ hydrogenation reactor containing 40% methanol and 60% water was fed into preheating zone at 180° C. at 2.5 mL/min to vaporize the methanol and water. The vapor was then introduced to the reactor at 50 PSI and a weight hourly space velocity of 5.0 $h^{-1}$. The resulting gas mixture containing mainly ethylene, propylene, and some other alkane and olefins was collected after gas-liquid separator and analyzed on GC-TCD. The liquid output containing water and unreacted methanol was collected from gas-liquid separator and analyzed on a GC-FID.

The SAPO catalyst was regenerated after the conversion of methanol dropped below 90%. The reactor was heated to 650° C. and the DI water was fed into reactor at 0.75 mL/min for 40 minutes. The reactor was then cooled down to 450° C. to resume methanol-to-olefin process.

TABLE 1

Comparison between commercial MTO process and
modified MTO process disclosed herein

|  | Methanol conversion | Ethylene/ Propylene (wt/wt) |
|---|---|---|
| Commercial process with SAPO-34 catalyst | >90% | 0.79 |
| Modified MTO process disclosed herein | >90% | 2.22 |

Figure 4:
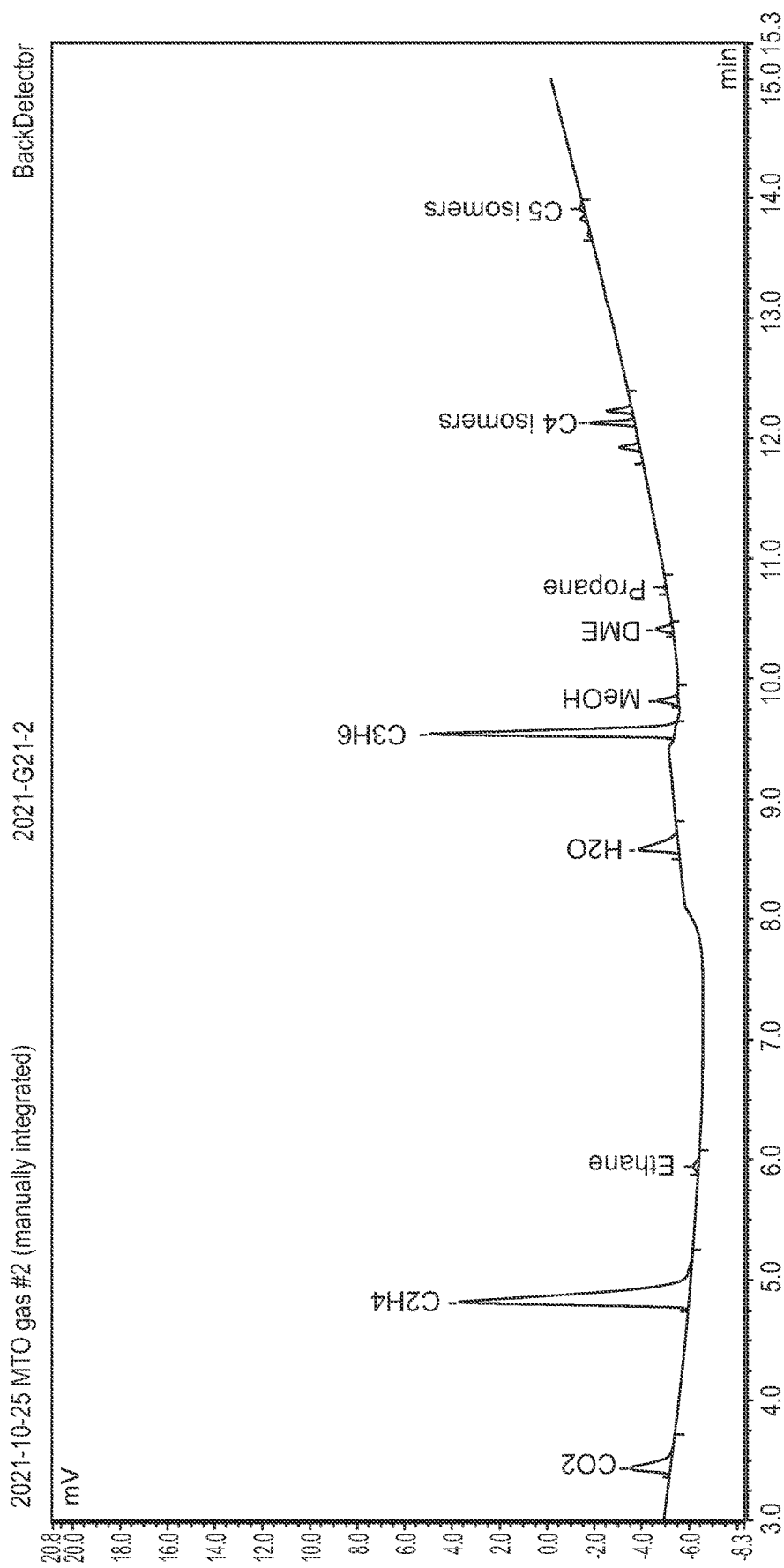
FIG. 4 shows a GC-FID chromatogram of the product from the modified MTO process disclosed herein, as described in Example 4.

FIG. 4 shows a GC-FID chromatogram of the product from the MTO process disclosed herein.

Example 5: Aromatic Formation from Propylene Oligomerization

Propylene was fed into a fixed bed flow reactor with 20 g of ZSM-5 catalyst (2 mm diameter with 10 mm length). The alumina was used as inert to pack the reactor. Propylene was fed into the reactor at 2.5 SCFH (1.2 SLPM) at 30 PSI for 10 minutes before slowly heating up the reactor to 250° C. The propylene was fed in at 2.5 SCFH (1.2 SLPM) for one hour, collecting 100 mL golden yellow liquid. The resulting liquid was collected from gas-liquid separator and analyzed with GC-FID.

Figure 5:
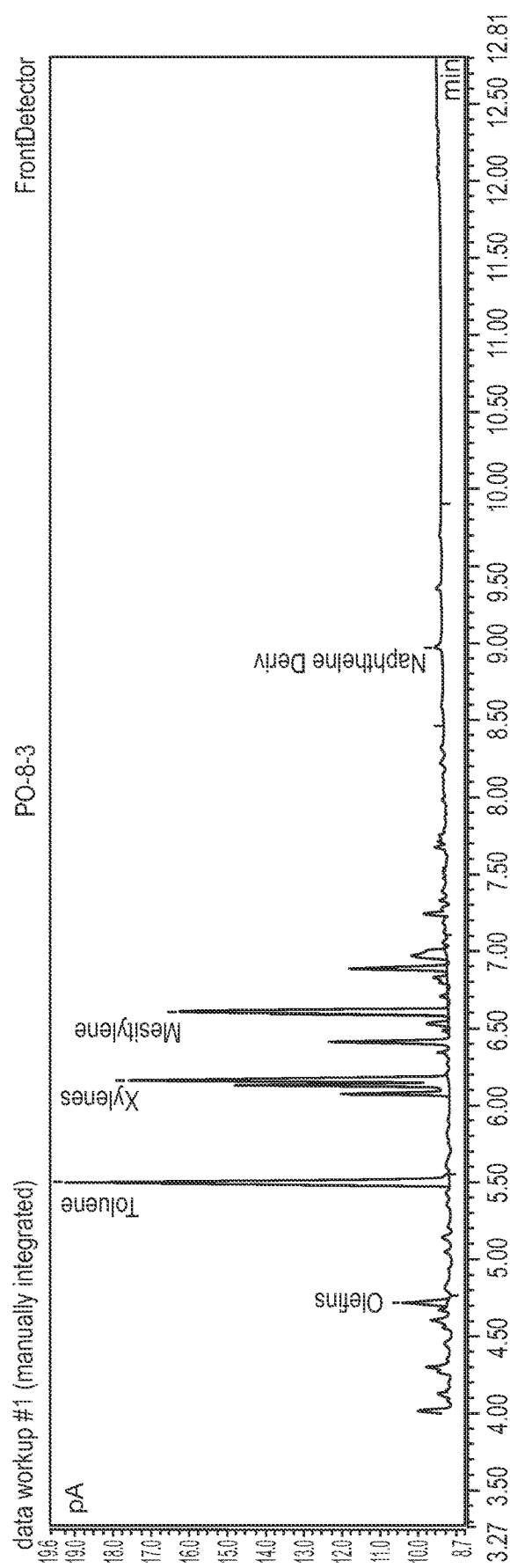
FIG. 5 shows a GC-FID chromatogram of propylene oligomerization product liquid described in Example 5.

FIG. 5 shows a GC-FID chromatogram of propylene oligomerization product liquid.

Example 6: Iso-Paraffin Formation from Paraffin Isomerization

To a 600 mL continuous stirred tank reactor was added 10 g of $AlCl_3$ and 50 mL of paraffin containing 98% linear n-Paraffin from $C_7$-$C_{28}$. The reactor was sealed and flashed with $H_2$ at 100 PSI for 3 times to remove residual air. The system was then pressurized with $H_2$ at 500 PSI and heated up to 150° C. with vigorous stirring for 6 hours. The reactor was then cooled down to room temperature and the pressure was released. The resulting light-yellow liquid was then collected and analyzed via GC-FID. 19% of n-paraffin was undergo isomerization to give iso-paraffin and cyclo-paraffin isomers.

Figure 6:
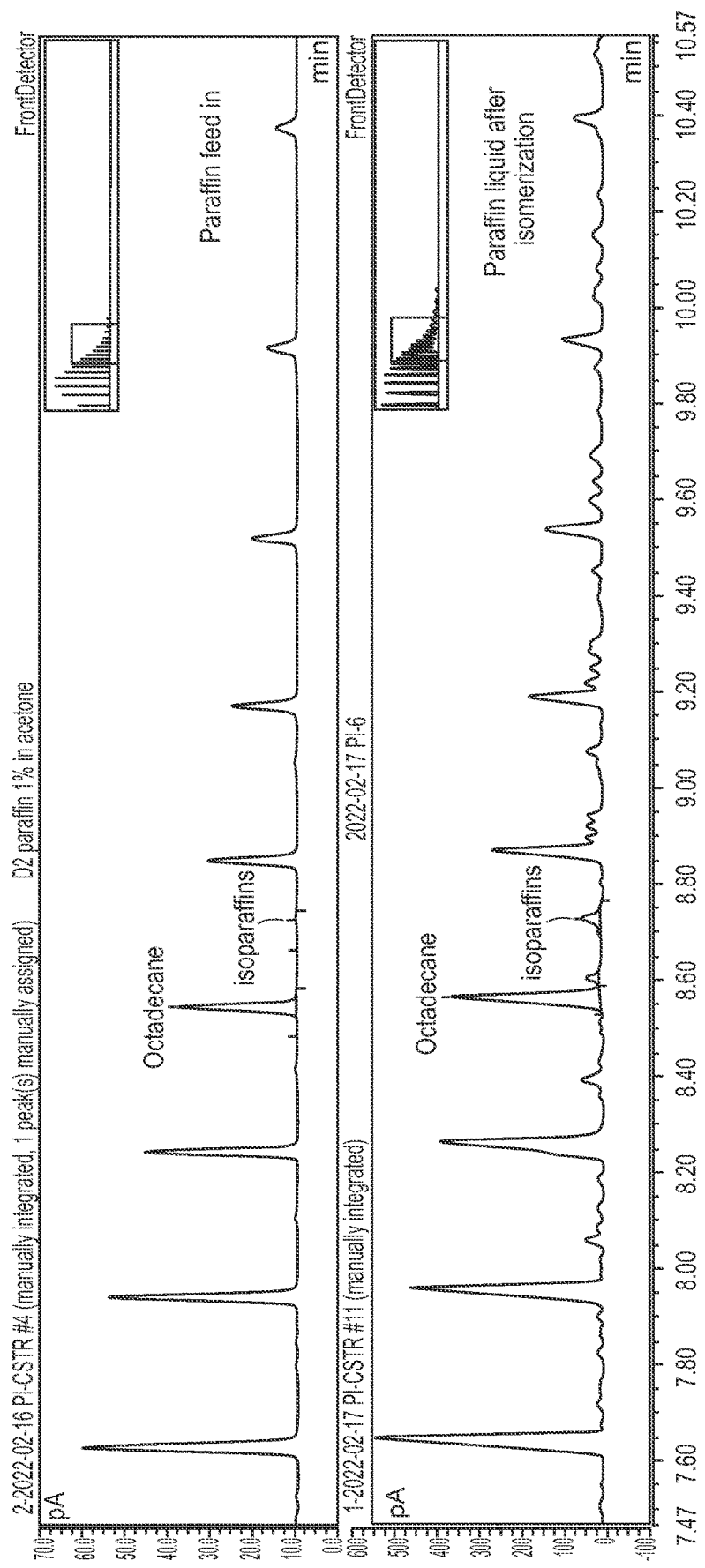
FIG. 6 shows a comparison of GC-FID chromatograms for paraffin liquid feed in and isomerization product.

FIG. 6 shows a comparison of GC-FID chromatograms for paraffin liquid feed in and isomerization product.

Example 7: Ethanol Production from Ethylene Hydration

To a 1 in diameter fixed bed reactor was added 15 g of catalyst containing phosphoric acid treated silica. Alumina was used as inert to pack the rest of the reactor. The system was sealed and flushed with $N_2$ for 20 minutes, before fed in ethylene at 150 PSI. The reactor was then slowly heat up to 250° C. The water was fed in to the reactor through a high-pressure syringe pump to maintain the steam/ethylene ratio at 2. The liquid was collected from liquid gas separator and analyzed on GC-FID to determine ethanol formation.

Figure 7:
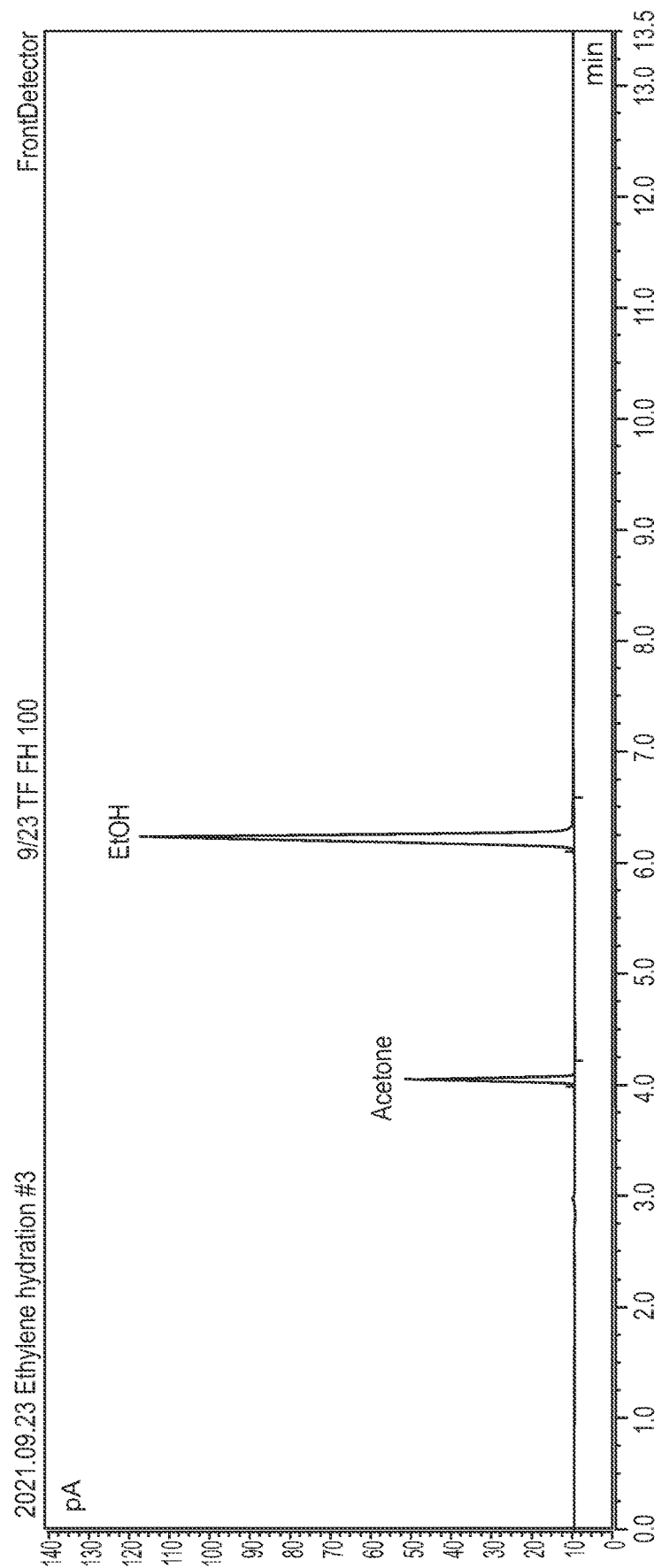
FIG. 7 shows a GC-FID chromatogram of ethylene hydrogenation liquid product.

FIG. 7 shows a GC-FID chromatogram of ethylene hydrogenation liquid product.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A system for the production of ethanol, comprising:
a $CO_2$ reduction reactor for converting a first gas mixture comprising CO2 and a reduction gas to a first product mixture comprising an alcohol product mixture comprising methanol; wherein the CO2 reduction reactor comprises a first catalyst;
a MTO reactor for dehydrating the alcohol product mixture into ethylene and a second product mixture comprising olefins and other hydrocarbons; wherein the MTO reactor comprises a second catalyst; and
a separator configured to separate ethylene from the second product mixture; and
an ethylene hydration reactor for hydrating the ethylene to form ethanol, wherein the ethylene hydration reactor comprises a fourth catalyst.

2. The system of claim 1, wherein the first catalyst comprises platinum, palladium, copper, cobalt, zinc, selenium, rhodium, iron, molybdenum, sulfur, oxygen, or alloys or chemical compounds thereof.

3. The system of claim 1, wherein the first catalyst comprises nanoparticles comprising CuZn, CuZnFeK, CuZnFeKC, CuZnFeAlK, CuZnFeNa, CuZnFeCoK, CuZnFeCoNaK, CuCoAl, CoMoSK, CuZnK, CuCoMn, RhRu, PdCuFe, Rh, or RhFeSi, optionally on an alumina support.

4. The system of claim 1, wherein the first catalyst comprises:
copper;
zinc;
one or more first elements selected from cobalt, nickel, or iron;
aluminum; and
oxygen.

5. The system of claim 2, wherein the first catalyst comprises cobalt, copper, zinc, oxygen, and alumina.

6. The system of claim 1, wherein the first catalyst comprises cobalt, copper, zinc, oxygen, alumina, and a Group IA metal.

7. The system of claim 1, wherein the first catalyst comprises cobalt, iron, copper, zinc, oxygen, alumina, and a Group IA metal.

8. The system of claim 1, wherein the first catalyst comprises copper, zinc, oxygen, and aluminum.

9. The system of claim 8, wherein the first catalyst is prepared from a mixture comprising copper oxide and zinc oxide.

10. The system of claim 8, wherein the first catalyst is prepared from a mixture comprising copper oxide, zinc oxide, and aluminum oxide in a copper oxide:zinc oxide: aluminum oxide ratio of about 63:27:10.

11. The system of claim 1, wherein the reduction gas is $H_2$ or a hydrocarbon.

12. The system of claim 1, wherein the first catalyst comprises CuZn.

13. The system of claim 1, wherein:
the first catalyst comprises a metal selected from the group consisting of: platinum, palladium, copper, cobalt, zinc, selenium, rhodium, iron, molybdenum, and any combination thereof;
the second catalyst is selected from a group consisting of: a crystalline zeolite, a silicoaluminophosphate, and any combination thereof; and
the fourth catalyst is selected from a group consisting of: a crystalline zeolite, a silicoaluminophosphate, any combination thereof.

14. The system of claim 13, wherein:
the second catalyst is selected from a group consisting of: SAPO-5, H-SAPO-34, ZSM-11, TNU-9, IM-5, ZSM-35, ZSM-22, ZSM-23, SSZ-13, UZM-12, UZM-9, UZM-5, RUB-13, ZSM-5, ZSM-34, and any combination thereof; and
the fourth catalyst is selected from a group consisting of: SAPO-5, H-SAPO-34, ZSM-11, TNU-9, IM-5, ZSM-35, ZSM-22, ZSM-23, SSZ-13, UZM-12, UZM-9, UZM-5, RUB-13, ZSM-5, ZSM-34, and any combination thereof.

15. The system of claim 1, wherein the second catalyst is selected from a group consisting of: a crystalline zeolite, a silicoaluminophosphate, and any combination thereof.

16. The system of claim 1, wherein the fourth catalyst is selected from a group consisting of: a crystalline zeolite, a silicoaluminophosphate, any combination thereof.

17. The system of claim 13, further comprising:
an oligomerization reactor for oligomerizing the olefin product mixture to a higher olefin product mixture comprising unsaturated paraffins and optionally aromatics; wherein the oligomerization reactor comprises a third catalyst,
wherein the third catalyst is a zeolite.

18. The system of claim 1, further comprising:
an oligomerization reactor for oligomerizing the olefin product mixture to a higher olefin product mixture comprising unsaturated paraffins and optionally aromatics; wherein the oligomerization reactor comprises a third catalyst,
wherein the third catalyst is a zeolite.

* * * * *